United States Patent [19]

Szarek et al.

[11] Patent Number: 5,869,469
[45] Date of Patent: Feb. 9, 1999

[54] PHOSPHONOCARBOXYLATE COMPOUNDS FOR TREATING AMYLOIDOSIS

[75] Inventors: Walter A. Szarek; Xianqi Kong, both of Kingston, Canada

[73] Assignee: Queen's University at Kingston, Kingston, Canada

[21] Appl. No.: 912,574

[22] Filed: Aug. 18, 1997

[51] Int. Cl.⁶ .................................................. A61K 31/66
[52] U.S. Cl. ............................................................ 514/120
[58] Field of Search .............................................. 514/120

[56] References Cited

U.S. PATENT DOCUMENTS

| | | | |
|---|---|---|---|
| 4,386,081 | 5/1983 | Helgstrand et al. | 424/212 |
| 4,591,583 | 5/1986 | Helgstrand et al. | 514/120 |
| 5,164,285 | 11/1992 | Kisilevsky et al. | 435/7.8 |
| 5,194,654 | 3/1993 | Hostetler et al. | 558/152 |
| 5,463,092 | 10/1995 | Hostetler et al. | 554/40 |

*Primary Examiner*—James H. Reamer
*Attorney, Agent, or Firm*—Lahive & Cockfield, LLP

[57] ABSTRACT

Therapeutic compounds and methods for modulating amyloid deposition in a subject, whatever its clinical setting, are described. Amyloid deposition is modulated by the administration to a subject of an effective amount of a therapeutic compound comprising a phosphonate group and a carboxylate group, or a pharmaceutically acceptable salt or ester thereof. In preferred embodiments, an interaction between an amyloidogenic protein and a basement membrane constituent is modulated.

25 Claims, No Drawings

PHOSPHONOCARBOXYLATE COMPOUNDS FOR TREATING AMYLOIDOSIS

BACKGROUND OF INVENTION

Amyloidosis refers to a pathological condition characterized by the presence of amyloid. Amyloid is a generic term referring to a group of diverse but specific extracellular protein deposits which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common x-ray diffraction and infrared spectra.

Amyloidosis can be classified clinically as primary, secondary, familial and/or isolated. Primary amyloidosis appears de novo without any preceding disorder. Secondary amyloidosis is that form which appears as a complication of a previously existing disorder. Familial amyloidosis is a genetically inherited form found in particular geographic populations. Isolated forms of amyloidosis are those that tend to involve a single organ system. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic angiopathy, neuritic plaques and neurofibrillary tangles, all of which have the characteristics of amyloids. In this case, the plaque and blood vessel amyloid is formed by the beta protein. Other systemic diseases such as adult-onset diabetes, complications of long-term hemodialysis and sequelae of long-standing inflammation or plasma cell dyscrasias are characterized by the accumulation of amyloids systemically. In each of these cases, a different amyloidogenic protein is involved in amyloid deposition.

SUMMARY OF THE INVENTION

This invention provides methods and compositions which are useful in the treatment of amyloidosis. The methods of the invention involve administering to a subject a therapeutic compound which inhibits amyloid deposition. Accordingly, the compositions and methods of the invention are useful for inhibiting amyloidosis in disorders in which amyloid deposition occurs. The methods of the invention can be used therapeutically to treat amyloidosis or can be used prophylactically in a subject susceptible to amyloidosis. Without wishing to be bound by theory, it is believed that the methods of the invention are based, at least in part, on inhibiting an interaction between an amyloidogenic protein and a constituent of basement membrane to inhibit amyloid deposition. The constituent of basement membrane can be a glycoprotein or proteoglycan, preferably heparan sulfate proteoglycan. In certain embodiments, a therapeutic compound used in the method of the invention preferably can interfere with binding of a basement membrane constituent to a target binding site on an amyloidogenic protein, thereby inhibiting amyloid deposition.

The invention relates to phosphonocarboxylate compounds, i.e., compounds which include a phosphonate group and a carboxylate group, or a pharmaceutically acceptable salt or ester thereof. In one embodiment, the method of the invention involves administering to a subject an effective amount of a therapeutic compound having the formula:

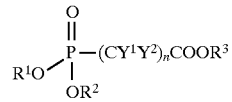

in which $R^1$ and $R^2$ are each independently hydrogen, an aliphatic group (preferably a branched or straight-chain aliphatic moiety having from 1 to 24 carbon atoms in the chain; or an unsubstituted or substituted cyclic aliphatic moiety having from 4 to 7 carbon atoms in the aliphatic ring; preferred aliphatic and cyclic aliphatic groups are alkyl groups, more preferably lower alkyl), an aryl group, a heterocyclic group, or a salt-forming cation; $R^3$ is hydrogen, lower alkyl, aryl, or a salt-forming cation; $Y^1$ and $Y^2$ are each independently hydrogen, halogen (e.g., F, Cl, Br, or I), lower alkyl, hydroxy, alkoxy, or aryloxy; and n is an integer from 0 to 12 (more preferably 0 or 1); such that amyloid deposition is modulated. In preferred embodiments, therapeutic compounds of the invention prevent or inhibit amyloid deposition in a subject to which the therapeutic compound is administered. Preferred therapeutic compounds for use in the invention include compounds in which both $R^1$ and $R^2$ are pharmaceutically acceptable salt-forming cations. It will be appreciated that the stoichiometry of an anionic compound to a salt-forming counterion (if any) will vary depending on the charge of the anionic portion of the compound (if any) and the charge of the counterion. In a particularly preferred embodiment, $R^1$, $R^2$ and $R^3$ are each independently a sodium, potassium or calcium cation. In certain embodiments in which at least one of $R^1$ and $R^2$ is an aliphatic group, the aliphatic group has between 1 and 10 carbons atoms in the straight or branched chain, and is more preferably a lower alkyl group. In other embodiments in which at least one of $R^1$ and $R^2$ is an aliphatic group, the aliphatic group has between 10 and 24 carbons atoms in the straight or branched chain. In certain preferred embodiments, n is 0 or 1; more preferably, n is 0. In certain preferred embodiments of the therapeutic compounds, $Y^1$ and $Y^2$ are each hydrogen.

The therapeutic compounds of the invention are administered to a subject by a route which is effective for modulation of amyloid deposition. Suitable routes of administration include subcutaneous, intravenous, intramuscular and intraperitoneal injection. The therapeutic compounds of the invention have been found to be effective when administered orally. Accordingly, a preferred route of administration is oral administration. The therapeutic compounds can be administered with a pharmaceutically acceptable vehicle.

The invention also provides methods for treating a disease state associated with amyloidosis by administering to a subject an effective amount of a therapeutic compound having the formula described supra, such that a disease state associated with amyloidosis is treated.

The invention provides methods for modulating amyloid deposition characterized by interaction between an amyloidogenic protein and a constituent of a basement membrane by administering to the subject an effective amount of a therapeutic compound having the formula described supra, such that modulation of amyloid deposition characterized by interaction between an amyloidogenic protein and a constituent of a basement membrane occurs.

The invention further provides pharmaceutical compositions for treating amyloidosis. The pharmaceutical compositions include a therapeutic compound of the invention in an amount effective to modulate amyloid deposition and a pharmaceutically acceptable vehicle.

The invention also provides packaged pharmaceutical compositions for treating amyloidosis. The packaged pharmaceutical compositions include a therapeutic compound of the invention and instructions for using the pharmaceutical composition for treatment of amyloidosis.

DETAILED DESCRIPTION OF INVENTION

This invention pertains to methods and compositions useful for treating amyloidosis. The methods of the invention involve administering to a subject a therapeutic compound which modulates amyloid deposition. "Modulation of amyloid deposition" is intended to encompass prevention of amyloid formation, inhibition of further amyloid deposition in a subject with ongoing amyloidosis and reduction of amyloid deposits in a subject with ongoing amyloidosis. Modulation of amyloid deposition is determined relative to an untreated subject or relative to the treated subject prior to treatment. In certain embodiments, amyloid deposition can be modulated by modulating an interaction between an amyloidogenic protein and a constituent of basement membrane.

"Basement membrane" refers to an extracellular matrix comprising glycoproteins and proteoglycans, including laminin, collagen type IV, fibronectin and/or heparan sulfate proteoglycan (HSPG). In one embodiment, amyloid deposition is modulated by interfering with an interaction between an amyloidogenic protein and a sulfated glycosaminoglycan such as HSPG. Sulfated glycosaminoglycans are known to be present in all types of amyloids (see Snow, A. D. et al. (1987) Lab. Invest. 56:120–123) and amyloid deposition and HSPG deposition occur coincidentally in animal models of amyloidosis (see Snow, A. D. et al. (1987) Lab. Invest. 56:665–675). In preferred embodiments of the methods of the invention, molecules which have a similar structure to a sulfated glycosaminoglycan are used to modulate interaction between an amyloidogenic protein and basement membrane constituent. In particular, the therapeutic compounds of the invention preferably comprise at least one phosphonate group (or phosphonic ester), or a functional equivalent thereof, and a carboxylate group (or carboxylic ester), provided that the compound includes at least one anionic group. The anionic groups(s) can optionally be covalently bound to a carrier (e.g., an aliphatic group, peptide or peptidomimetic, or the like). In addition to functioning as a carrier for the anionic functionality, the carrier molecule can enable the compound to traverse biological membranes and to be biodistributed without excessive or premature metabolism.

In one embodiment, the method of the invention includes administering to the subject an effective amount of a therapeutic compound which has at least one phosphonate group or phosphonic ester group. The therapeutic compound is preferably capable of modulating interaction between an amyloidogenic protein and a glycoprotein or proteoglycan constituent of a basement membrane to thus modulate amyloid deposition. The therapeutic compound has the formula:

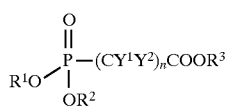

in which $R^1$ and $R^2$ are each independently hydrogen, an aliphatic group (preferably a branched or straight-chain aliphatic moiety having from 1 to 24 carbon atoms, more preferably 10–24 carbon atoms, in the chain; or an unsubstituted or substituted cyclic aliphatic moiety having from 4 to 7 carbon atoms in the aliphatic ring), an aryl group, a heterocyclic group, or a salt-forming cation; $R^3$ is hydrogen, lower alkyl, aryl, or a salt-forming cation; $Y^1$ and $Y^2$ are each independently hydrogen, halogen (e.g., F, Cl, Br, or I), lower alkyl, hydroxy, alkoxy, or aryloxy; and n is an integer from 0 to 12; such that amyloid deposition is modulated. In one preferred embodiment, therapeutic compounds of the invention prevent or inhibit amyloid deposition in a subject to which the therapeutic compound is administered. Preferred therapeutic compounds for use in the invention include compounds in which both $R^1$ and $R^2$ arepharmaceutically acceptable salt-forming cations. In a particularly preferred embodiment, $R^1$, $R^2$ and $R^3$ are each independently a sodium, potassium or calcium cation, and n is 0. In certain preferred embodiments of the therapeutic compounds, $Y^1$ and $Y^2$ are each hydrogen.

The $R^1$, $R^2$, $R^3$, $Y^1$ and $Y^2$ groups are each independently selected such that the biodistribution of the compound for an intended target site is not prevented while maintaining activity of the compound. For example, the number of anionic groups (and the overall charge on the therapeutic compound) should not be so great as to inhibit traversal of an anatomical barrier, such as a cell membrane, or entry across a physiological barrier, such as the blood-brain barrier, in situations where such properties are desired. For example, it has been reported that esters of phosphonoformate have biodistribution properties different from, and in some cases superior to, the biodistribution properties of phosphonoformate (see, e.g., U.S. Pat. Nos. 4,386,081 and 4,591,583 to Helgstrand et al., and U.S. Pat. Nos. 5,194,654 and 5,463,092 to Hostetler et al.). Thus, in certain embodiments, at least one of $R^1$ and $R^2$ is an aliphatic group (more preferably an alkyl group), in which the aliphatic group has between 10 and 24 carbons atoms in the straight or branched chain. The number, length, and degree of branching of the aliphatic chains can be selected to provide a desired characteristic, e.g., lipophilicity. In other embodiments, at least one of $R^1$ and $R^2$ is an aliphatic group (more preferably an alkyl group), in which the aliphatic group has between 1 and 10 carbons atoms in the straight or branched chain. Again, the number, length, and degree of branching of the aliphatic chains can be selected to provide a desired characteristic, e.g., lipophilicity or ease of ester cleavage by enzymes. In this embodiment, a preferred aliphatic group is an ethyl group.

An anionic group (i.e., a phosphonate or carboxylate group) of a therapeutic compound of the invention is a negatively charged moiety that, in certain preferred embodiments, can modulate interaction between an amyloidogenic protein and a glycoprotein or proteoglycan constituent of a basement membrane to thus modulate amyloid deposition.

The ability of a therapeutic compound of the invention to modulate interaction between an amyloidogenic protein and a glycoprotein or proteoglycan constituent of a basement membrane can be assessed by an in vitro binding assay, such as that described in the Exemplification or in U.S. Pat. No. 5,164,295 by Kisilevsky et al. Briefly, a solid support such as a polystyrene microtiter plate is coated with an amyloidogenic protein (e.g., serum amyloid A protein or β-amyloid precursor protein (β-APP)) and any residual hydrophobic surfaces are blocked. The coated solid support is incubated with various concentrations of a constituent of basement membrane, preferably HSPG, either in the presence or absence of a compound to be tested. The solid support is washed extensively to remove unbound material. The binding of the basement membrane constituent (e.g., HSPG) to the amyloidogenic protein (e.g., β-APP) is then measured using an antibody directed against the basement membrane constituent which is conjugated to a detectable substance (e.g., an enzyme, such as alkaline phosphatase) by detecting the detectable substance. A compound which modulates an interaction between an amyloidogenic protein and a glycoprotein or proteoglycan constituent of a basement membrane will reduce the amount of substance detected (e.g., will inhibit the amount of enzyme activity detected).

Preferably, a therapeutic compound of the invention interacts with a binding site for a basement membrane glycoprotein or proteoglycan in an amyloidogenic protein and thereby modulates the binding of the amyloidogenic protein to the basement membrane constituent. Basement membrane glycoproteins and proteoglycans include laminin, collagen type IV, fibronectin and heparan sulfate proteoglycan (HSPG). In a preferred embodiment, the therapeutic compound inhibits an interaction between an amyloidogenic protein and HSPG.

In certain embodiments, a therapeutic compound of the invention comprises a cation (i.e., in certain embodiments, at least one of $R^1$, $R^2$ or $R^3$ is a cation). If the cationic group is hydrogen, $H^+$, then the compound is considered an acid, e.g., phosphonoformic acid. If hydrogen is replaced by a metal ion or its equivalent, the compound is a salt of the acid. Pharmaceutically acceptable salts of the therapeutic compound are within the scope of the invention. For example, at least one of $R^1$, $R^2$ or $R^3$ can be a pharmaceutically acceptable alkali metal (e.g., Li, Na, or K), ammonium cation, alkaline earth cation (e.g., $Ca^{2+}$, $Ba^{2+}$, $Mg^{2+}$), higher valency cation, or polycationic counter ion (e.g., a polyammonium cation). (See, e.g., Berge et al. (1977) "Pharmaceutical Salts", *J Pharm. Sci.* 66:1–19). It will be appreciated that the stoichiometry of an anionic compound to a salt-forming counterion (if any) will vary depending on the charge of the anionic portion of the compound (if any) and the charge of the counterion. Preferred pharmaceutically acceptable salts include a sodium, potassium or calcium salt, but other salts are also contemplated within their pharmaceutically acceptable range.

The term "pharmaceutically acceptable esters" refers to the relatively non-toxic, esterified products of the compounds of the present invention. These esters can be prepared in situ during the final isolation and purification of the compounds or by separately reacting the purified compound in its free acid form or hydroxyl with a suitable esterifying agent; either of which are methods known to those skilled in the art. Carboxylic acids and phosphonic acids can be converted into esters according to methods well known to one of ordinary skill in the art, e.g., via treatment with an alcohol in the presence of a catalyst. A preferred ester group (e.g., when $R^3$ is lower alkyl) is an ethyl ester group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 4–7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "alkoxy", as used herein, refers to a moiety having the structure—O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Preferred aryl groups include unsubstituted and substituted phenyl groups.

The term "aryloxy", as used herein, refers to a group having the structure—O-aryl, in which the aryl moiety is as defined above.

In a preferred embodiment, $R^1$ or $R^2$ can be (for at least one occurrence) a long-chain aliphatic moiety. The term "long-chain aliphatic moiety" as used herein, refers to a moiety having a straight or branched chain aliphatic moiety (e.g., an alkyl or alkenyl moiety) having from 10 to 24 carbons in the aliphatic chain, e.g., the long-chain aliphatic moiety is an aliphatic chain of a fatty acid (preferably a naturally-occurring fatty acid). Representative long-chain aliphatic moieties include the aliphatic chains of stearic acid, oleic acid, linolenic acid, and the like.

The therapeutic compound of the invention can be administered in a pharmaceutically acceptable vehicle. As used herein "pharmaceutically acceptable vehicle" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

In certain embodiments, the therapeutic compound of the invention can be represented by the formula:

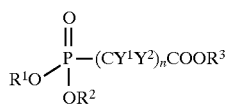

in which $R^1$ and $R^2$ are each independently hydrogen, an aliphatic group (preferably a branched or straight-chain aliphatic moiety having from 1 to 24 carbon atoms, more preferably 10–24 carbon atoms, in the chain; or an unsubstituted or substituted cyclic aliphatic moiety having from 4 to 7 carbon atoms in the aliphatic ring), an aryl group, a heterocyclic group, or a salt-forming cation; $R^3$ is hydrogen, lower alkyl, aryl, or a salt-forming cation; $Y^1$ and $Y^2$ are each independently hydrogen, halogen (e.g., F, Cl, Br, or I), lower alkyl, hydroxy, alkoxy, or aryloxy; and n is an integer from 0 to 12; such that amyloid deposition is modulated. In one preferred embodiment, therapeutic compounds of the invention prevent or inhibit amyloid deposition in a subject to which the therapeutic compound is administered. Preferred therapeutic compounds for use in the invention include compounds in which both $R^1$ and $R^2$ arepharmaceutically acceptable salt-forming cations. In a particularly preferred embodiment, $R^1$, $R^2$ and $R^3$ are each independently a sodium, potassium or calcium cation, and n is 0. In certain preferred embodiments of the therapeutic compounds, $Y^1$ and $Y^2$ are each hydrogen. Particularly preferred therapeutic compounds are salts of phosphonoformate. Trisodium phosphonoformate (foscarnet sodium or Foscavir®) is commercially available (e.g., from Astra), and its clinical pharmacology has been investigated (see, e.g., "Physician's Desk Reference", 51st Ed., pp. 541–545 (1997)).

A further aspect of the invention includes pharmaceutical compositions for treating amyloidosis. The therapeutic compounds in the methods of the invention, as described hereinbefore, can be incorporated into a pharmaceutical composition in an amount effective to modulate amyloidosis in a pharmaceutically acceptable vehicle.

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a phosphonate or carboxylate, can be esterified, e.g., with an ethyl group or a fatty group, to yield a phosphonic or carboxylic ester. When the phosphonic or carboxylic ester is administered to a subject, the ester can be cleaved, enzymatically or non-enzymatically, reductively or hydrolytically, to reveal the anionic group. Such an ester can be cyclic, e.g., a cyclic phosphonate, or two or more anionic moieties may be esterified through a linking group. In a preferred embodiment, the prodrug is a phosphonate or carboxylate. An anionic group can be esterified with moieties (e.g., acyloxymethyl esters) which are cleaved to reveal an intermediate compound which subsequently decomposes to yield the active compound. Furthermore, an anionic moiety (e.g., a phosphonate or carboxylate) can be esterified to a group which is actively transported in vivo, or which is selectively taken up by target organs. The ester can be selected to allow specific targeting of the therapeutic moieties to particular organs, as described below for carrier moieties.

Carrier moieties useful in the present invention may also include moieties which allow the therapeutic compound to be selectively delivered to a target organ or organs. For example, if delivery of a therapeutic compound to the brain is desired, the carrier molecule may include a moiety capable of targeting the therapeutic compound to the brain, by either active or passive transport (a "targeting moiety"). Illustratively, the carrier molecule may include a redox moiety, as described in, for example, U.S. Pat. Nos. 4,540, 564 and 5,389,623, both to Bodor. These patents disclose drugs linked to dihydropyridine moieties which can enter the brain, where they are oxidized to a charged pyridinium species which is trapped in the brain. Thus, drug accumulates in the brain. Other carrier moieties include compounds, such as amino acids or thyroxine, which can be passively or actively transported in vivo. Such a carrier moiety can be metabolically removed in vivo, or can remain intact as part of an active compound. Structural mimics of amino acids (and other actively transported moieties), including peptidomimetics, are also useful in the invention. As used herein, the term "peptidomimetic" is intended to include peptide analogs which serve as appropriate substitutes for peptides in interactions with e.g., receptors and enzymes. The peptidomimetic must possess not only affinity, but also efficacy and substrate function. That is, a peptidomimetic exhibits function(s) of a peptide, without restriction of structure. Peptidomimetics, methods for their preparation and use are described in Morgan et al., "Approaches to the discovery of non-peptide ligands for peptide receptors and peptidases," In *Annual Reports in Medicinal Chemistry* (Virick, F. J., ed.) pp. 243–253, Academic Press, San Diego, Calif. (1989), the contents of which are incorporated herein by reference. Many targeting moieties are known, and include, for example, asialoglycoproteins (see, e.g. Wu, U.S. Pat. No. 5,166,320) and other ligands which are transported into cells via receptor-mediated endocytosis (see below for further examples of targeting moieties which may be covalently or non-covalently bound to a carrier molecule). Furthermore, the therapeutic compounds of the invention may bind to amyloidogenic proteins in the circulation and thus be transported to the site of action.

The targeting and prodrug strategies described above can be combined to produce a compound that can be transported as a prodrug to a desired site of action and then unmasked to reveal an active compound.

In the methods of the invention, amyloid deposition (e.g., deposition of β-amyloid) in a subject is modulated by administering a therapeutic compound of the invention to the subject. The term "subject" is intended to include living organisms in which amyloidosis can occur. Examples of subjects include humans, monkeys, cows, sheep, goats, dogs, cats, mice, rats, and transgenic species thereof. Administration of the compositions of the present invention to a subject to be treated can be carried out using known procedures, at dosages and for periods of time effective to modulate amyloid deposition in the subject. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to modulate amyloid deposition in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., phosphonoformic acid, trisodium salt) is between 5 and 500 mg/kg of body weight/per day. In an aqueous composition, preferred concentrations for the active compound (i.e., the therapeutic compound that can modulate amyloid deposition) are between 5 and 500 mM, more preferably between 10 and 100 mM, and still more preferably between 20 and 50 mM.

The therapeutic compounds of the invention can be effective when administered orally. Accordingly, a preferred route of administration is oral administration. Alternatively, the active compound may be administered by other suitable routes such as subcutaneous, intravenous, intramuscular or intraperitoneal administration, and the like (e.g. by injection). Depending on the route of administration, the active compound may be coated in a material to protect the compound from the action of acids and other natural conditions which may inactivate the compound.

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBSLett.* 357:140; M. Owais et al. (1995) *Antimicrob. Agents Chemother.* 39:180); surfactant protein A receptor (Briscoe et al. (1995) *Am. J Physiol.* 1233:134); gpl20 (Schreier et al. (1994) *J Biol. Chem.* 269:9090); see also K. Keinanen; M. L. Laukkanen (1994) *FEBSLett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

Delivery and in vivo distribution can also be affected by alteration of an anionic group of compounds of the invention. For example, anionic groups such as phosphonate or carboxylate can be esterified to provide compounds with desirable pharmocokinetic, pharmacodynamic, biodistributive, or other properties. Exemplary compounds include phosphonoformate trisodium salt (Foscarnet, Foscavir), phosphonoacetate, trisodium salt, and pharmaceutically acceptable salts or esters thereof.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of amyloid deposition in subjects.

Therapeutic compositions can be administered in time-release or depot form, to obtain sustained release of the therapeutic compounds over time. The therapeutic compounds of the invention can also be administered transdermally (e.g., by providing the therapeutic compound, with a suitable carrier, in patch form).

Active compounds are administered at a therapeutically effective dosage sufficient to modulate amyloid deposition in a subject. A "therapeutically effective dosage" preferably modulates amyloid deposition by at least about 20%, more preferably by at least about 40%, even more preferably by at least about 60%, and still more preferably by at least about 80% relative to untreated subjects. The ability of a compound to modulate amyloid deposition can be evaluated in model systems that may be predictive of efficacy in modulating amyloid deposition in human diseases, such as animal model systems known in the art (including, e.g., the method described in PCT Publication WO 96/28187) or by in vitro methods, e.g., the method of Chakrabartty, described in PCT Publication WO 97/07402, or the assay described in Example 1, infra. Alternatively, the ability of a compound to modulate arnyloid deposition can be evaluated by examining the ability of the compound to modulate an interaction between an amyloidogenic protein and a basement membrane constituent, e.g., using a binding assay such as that described hereinbefore. Furthermore, the amount or distribution of amyloid deposits in a subject can be non-invasively monitored in vivo, for example, by use of radio-labelled tracers which can associate with amyloid deposits, followed by scintigraphy to image the amyloid deposits (see, e.g., Aprile, C. et al., *Eur. J Nucl. Med.* 22:1393 (1995); Hawkins, P. N., *Baillieres Clin. Rheumatol.* 8:635 (1994); and references cited therein). Thus, for example, the amyloid load of a subject can be evaluated after a period of treatment according to the methods of the invention and compared to the amyloid load of the subject prior to beginning therapy with a therapeutic compound of the invention, to determine the effect of the therapeutic compound on amyloid deposition in the subject.

The method of the invention is useful for treating amyloidosis associated with any disease in which amyloid deposition occurs. Clinically, amyloidosis can be primary, secondary, familial or isolated. Amyloids have been categorized by the type of amyloidogenic protein contained within the amyloid. Non-limiting examples of amyloids which can be modulated, as identified by their amyloidogenic protein, are as follows (with the associated disease in parentheses after the amyloidogenic protein): β-amyloid (Alzheimer's disease, Down's syndrome, hereditary cerebral hemorrhage amyloidosis [Dutch]); amyloid A (reactive [secondary] amyloidosis, familial Mediterranean Fever, familial amyloid nephropathy with urticaria and deafness [Muckle-Wells syndrome]); amyloid κ L-chain or amyloid λ L-chain (idiopathic [primary], myeloma or macroglobulinemia-associated); Aβ2M (chronic hemodialysis); ATTR (familial amyloid polyneuropathy [Portuguese, Japanese, Swedish], familial amyloid cardiomyopathy [Danish], isolated cardiac amyloid, systemic senile amyloidosis); AIAPP or amylin (adult onset diabetes, insulinoma); atrial naturetic factor (isolated atrial amyloid); procalcitonin (medullary carcinoma of the thyroid); gelsolin (familial amyloidosis [Finnish]); cystatin C (hereditary cerebral hemorrhage with amyloidosis [Icelandic]); AApoA-I (familial amyloidotic polyneuropathy [Iowa]); AApoA-II (accelerated senescence in mice); fibrinogen-associated amyloid; lysozyme-associated amyloid; and AScr or PrP-27 (Scrapie, Creutzfeldt-Jacob disease, Gerstmann-Straussler-Scheinker syndrome, bovine spongiform encephalitis).

Phosphonate compounds for use in the methods of the invention are commercially available and/or can be synthesized by standard techniques known in the art. In general, phosphonic esters can be prepared from the corresponding phosphonic acid by standard methods. Similarly, carboxylic esters can be prepared from the free carboxylic acid by standard techniques (for a reference to esterification techniques, see, e.g., R. Larock, "Comprehensive Organic Transformations," VCH Publishers (1989)).

EXAMPLE I

It is known that amyloidogenic peptides or proteins which have formed amyloid deposits or plaques have a significant amount of β-sheet secondary structure, while the unaggregated peptide or protein generally has less β-sheet structure. It is believed that the ability of a candidate therapeutic compound to prevent the formation of β-sheet secondary structure in vitro may be correlated with the ability of the compound to inhibit amyloidogenesis in vivo. Accordingly, phosphonate compounds were assayed for ability to prevent the formation of β-sheet secondary structure in an in vitro circular dichroism (CD) assay.

Aβ is a 40 amino acid protein associated with Alzheimer's disease. Aβ peptide was prepared and purified as described in Fraser, P. E. et al., *Biochemistry* 31, 10716 (1992). Briefly, the peptide was synthesized by standard solid-phase techniques and purified by HPLC according to well known procedures.

All CD experiments were performed on a commercially available instrument. The cell was maintained at 25° C. using a circulating water bath. Computer-averaging of traces was performed to improve signal-to-noise ratios. The solvent signal was subtracted. CD experiments were performed for each test compound according to the following procedure:

A stock solution of purified peptide was made by dissolving the peptide in phosphate-buffered saline (PBS) to a concentration of 2 mg/ml. A test solution was made for each potential therapeutic agent (test compound) as shown below:

| | |
|---|---|
| Aβ stock solution | 25 µl |
| Test compound (20 mg/ml) | 2.5 µl |
| Distilled water | 2.5 µl |
| 10 mM Tris-HCl buffer, pH 7 | 370 µl |

The control sample had no test compound, and a total of 5 µl distilled water was added. The test solution was incubated for either 0 or 24 hours at 37° C. before CD measurement. The size minimum in the CD spectrum at 218 nm is believed to be diagnostic of the presence of β-pleated sheet. Comparison of the minimum at 218 nm of a candidate compound, compared to the minimum of a control sample, is believed to be indicative of the ability of the candidate compound to inhibit the formation of β-pleated sheet.

Using this assay, several candidate compounds were tested. Phosphonoformate sodium salt (foscarnet sodium) was found to significantly and reproducibly reduce the amount of β-sheet formation, as measured by the CD assay. Thus, phosphonoformate is believed to be an inhibitor of amyloid deposition. 2-carboxyethoxyethylphosphonic acid did not appear to prevent β-pleated sheet formation in this model system.

In a preliminary result in a different assay system (in which the candidate compound and amyloid peptide were incubated together overnight, followed by centrifugation and determination of the amount of soluble peptide), phosphonoformate trisodium salt was found to have little effect on amyloid peptide solubility; it is believed that the buffer composition may have interfered with the ability of the compound to inhibit amyloid deposition.

The neurotoxicity of phosphonoformate trisodium salt was investigated in cortical/hippocampal neuronal cultures; no significant toxicity was noted at concentrations ranging from $10^{-7}$M to $10^{-4}$M.

The contents of all references, issued patents, and published patent applications cited throughout this application are hereby incorporated by reference.

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for modulating amyloid deposition in a subject, comprising administering to a subject an effective amount of a therapeutic compound such that modulation of amyloid deposition occurs, wherein the therapeutic compound has the formula:

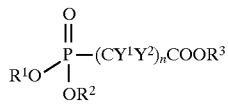

in which $R^1$ and $R^2$ are each independently hydrogen, an aliphatic group, an aryl group, a heterocyclyl group, or a salt-forming cation;

$R^3$ is hydrogen, lower alkyl, aryl or a salt-forming cation;

$Y^1$ and $Y^2$ are each independently hydrogen, halogen, lower alkyl, hydroxy, alkoxy, or aryloxy; and n is an integer from 0 to 12.

2. The method of claim 1, wherein $R^1$ and $R^2$ are each a pharmaceutically acceptable salt-forming cation.

3. The method of claim 2, in which $R^1$, $R^2$ and $R^3$ are each independently a sodium, potassium or calcium cation.

4. The method of claim 3, wherein n is 0.

5. The method of claim 1, wherein at least one of $R^1$ and $R^2$ is a long-chain aliphatic moiety.

6. The method of claim 5, wherein $R^3$ is a lower alkyl group.

7. The method of claim 1, wherein $Y^1$ and $Y^2$ are each hydrogen.

8. The method of claim 1, wherein the therapeutic compound is administered orally.

9. The method of claim 1, further comprising administering the therapeutic compound in a pharmaceutically acceptable vehicle.

10. The method of claim 1, wherein administering the therapeutic compound to the subject inhibits amyloid deposition in the subject.

11. A method for treating a disease state associated with amyloidosis, comprising:

administering to a subject an effective amount of a therapeutic compound such that a disease state associated with amyloidosis is treated, wherein the therapeutic compound has the formula

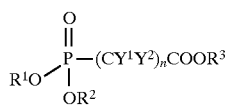

in which $R^1$ and $R^2$ are each independently hydrogen, an aliphatic group, an aryl group, a heterocyclyl group, or a salt-forming cation;

$R^3$ is hydrogen, lower alkyl, aryl or a salt-forming cation;

$Y^1$ and $Y^2$ are each independently hydrogen, halogen, lower alkyl, hydroxy, alkoxy, or aryloxy; and n is an integer from 0 to 12.

12. The method of claim 11, wherein said disease state is amyloid deposition associated with Alzheimer's disease.

13. The method of claim 11, wherein $R^1$ and $R^2$ are each a pharmaceutically acceptable salt-forming cation.

14. The method of claim 13, in which $R^1$, $R^2$ and $R^3$ are each independently a sodium, potassium or calcium cation.

15. The method of claim 14, wherein n is 0.

16. The method of claim 11, wherein at least one of $R^1$ and $R^2$ is a long-chain aliphatic moiety.

17. The method of claim 16, wherein $R^3$ is a lower alkyl group.

18. The method of claim 11, wherein $Y^1$ and $Y^2$ are each hydrogen.

19. The method of claim 11, wherein the therapeutic compound is administered orally.

20. The method of claim 11, further comprising administering the therapeutic compound in a pharmaceutically acceptable vehicle.

21. A method for modulating amyloid deposition in a subject in which said amyloid deposition is characterized by interaction between an amyloidogenic protein and a constituent of a basement membrane, the method comprising administering to the subject an effective amount of a therapeutic compound such that modulation of amyloid deposition characterized by interaction between an amyloidogenic protein and a constituent of a basement membrane occurs, wherein the therapeutic compound has the formula:

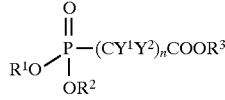

in which $R^1$ and $R^2$ are each independently hydrogen, an aliphatic group, an aryl group, a heterocyclyl group, or a salt-forming cation;

$R^3$ is hydrogen, lower alkyl, aryl or a salt-forming cation;

$Y^1$ and $Y^2$ are each independently hydrogen, halogen, lower alkyl, hydroxy, alkoxy, or aryloxy; and n is an integer from 0 to 12.

22. The method of claim 21, wherein $R^1$ and $R^2$ are each a pharmaceutically acceptable salt-forming cation.

23. The method of claim 22, in which $R^1$, $R^2$ and $R^3$ are each independently a sodium, potassium or calcium cation.

24. The method of claim 23, wherein n is 0.

25. The method of claim 21, wherein at least one of $R^1$ and $R^2$ is a long-chain aliphatic moiety.

* * * * *